United States Patent
Perrott et al.

(10) Patent No.: US 6,505,930 B1
(45) Date of Patent: *Jan. 14, 2003

(54) SPECTACLES FRAMES FOR SHAPED LENS ELEMENTS

(75) Inventors: Colin Maurice Perrott, Mount Barker (AU); Michael Alan Morris, Santa Rosa, CA (US)

(73) Assignee: Sola International Holdings, Ltd., South Lonsdale (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/830,050

(22) PCT Filed: Oct. 21, 1998

(86) PCT No.: PCT/AU98/00872

§ 371 (c)(1),
(2), (4) Date: Jul. 18, 2001

(87) PCT Pub. No.: WO00/23021

PCT Pub. Date: Apr. 27, 2000

(51) Int. Cl.⁷ .................................................. G02C 5/00
(52) U.S. Cl. ....................................... 351/41; 351/154
(58) Field of Search ........................... 351/41, 44, 159, 351/154

(56) References Cited

U.S. PATENT DOCUMENTS

| | | |
|---|---|---|
| 1,918,999 A | 7/1933 | Wells |
| 1,942,400 A | 1/1934 | Glancy |
| 4,577,942 A | 3/1986 | Frieder et al. |
| 4,778,266 A | 10/1988 | Maitenaz |
| 5,094,520 A | 3/1992 | Reshef et al. |
| 5,426,473 A | 6/1995 | Riehm |
| 5,483,303 A | 1/1996 | Hirschman |
| 5,541,674 A | 7/1996 | Jannard |
| 5,689,323 A * | 11/1997 | Houston et al. ............... 351/41 |
| 5,719,655 A | 2/1998 | Peschel et al. |
| 5,764,332 A | 6/1998 | Kranhouse |
| 5,774,201 A * | 6/1998 | Tackles ....................... 351/159 |
| 5,805,261 A | 9/1998 | Houston et al. |
| 5,825,455 A | 10/1998 | Fecteau et al. |
| 6,142,624 A | 11/2000 | Morris et al. |
| 6,334,681 B1 * | 1/2002 | Perrott et al. ................ 351/159 |

FOREIGN PATENT DOCUMENTS

| | | |
|---|---|---|
| FR | 1509090 | 11/1966 |
| FR | 83 03673 | 9/1984 |
| GB | 680400 | 1/1951 |
| GB | 1 509 583 | 7/1975 |
| WO | WO 79/00548 | 8/1979 |
| WO | WO 91/17468 | 11/1991 |
| WO | WO 97/21138 | 6/1997 |

OTHER PUBLICATIONS

M. Jalie; The Principles of Ophthalmic Lenses; Jan. 1972; pp. 1–29; Chapter 4, pp. 30–33; pp. 462–469; and pp. 151 & 152.; Fourth Edition; The Association of British Opticians, London England.

* cited by examiner

*Primary Examiner*—Huy Mai
(74) *Attorney, Agent, or Firm*—Burns, Doane, Swecker & Mathis, LLP

(57) ABSTRACT

The disclosure relates to spectacle frames including frames adapted to engage ovaline edges of lens elements having a toroidal or changing base curvature. In a preferred embodiment the frame shape corresponds to the edge of front surfaces of a pair of lens elements having a high curvature which is common to various prescriptions.

41 Claims, 6 Drawing Sheets

SPECTACLES FRAMES FOR SHAPED LENS ELEMENTS

FIELD OF THE INVENTION

The present invention relates to spectacle frames of the wrap-around or shield type, in particular frames adapted to receive optical lens of unconventional shape, and to optical lens elements for mounting in frames.

BACKGROUND AND OBJECTS OF THE INVENTION

It is known in the prior art to manufacture non-corrective eyeglasses such as sunglasses or protective eyeglasses having wrap-around segments designed to shield the eye from incident light, wind, and foreign objects in the temporal vision field of the wearer.

SUMMARY OF THE INVENTION AND PREFERRED EMBODIMENTS

Visible light and light in the UV region may enter the eye from angles as high as 100° from the line of sight.

It has not been possible, however, in prior art sunglasses or protective eyeglasses, to provide such spectacles with significant refractive power, whilst maintaining a cosmetically acceptable appearance. The radius of curvature required to provide an ophthalmic lens including a prescription surface is such that the spectacles would produce a bug-eyed appearance, which would be cosmetically unacceptable.

Further, in International Patent Application PCT/AU97/00188 "Improved Single Vision Lenses", Applicants disclose an optical lens element including a front and back surface, at least one surface being continuous, and forming a prescription (Rx) zone and a peripheral temporal zone for providing a shield in the area of the temples, which zones are smoothly blended to avoid a prismatic jump from the Rx zone to the temporal zone.

In International Patent Application. PCT/AU98/00274 "Lenses and Spectacles Bearing Lenses", to Applicants, the entire disclosure of which is incorporated herein by reference, Applicants disclose an ophthalmic article including an optical lens element including a front and back surface, at least one surface being continuous, and forming a prescription (Rx) zone and optionally a non-prescription peripheral temporal zone, at least one surface exhibiting a change of base curve across the field of vision of the wearer; the front and/or back surface bearing a surface correction to at least partially adjust for optical errors.

Whilst such lenses are a significant improvement, it is necessary to provide spectacle frames which will receive such unusually shaped lenses.

It is accordingly an object of the present invention to overcome, or at least alleviate, one or more of the difficulties and deficiencies related to the prior art.

Accordingly, in a first aspect of the present invention there is provided a spectacle frame shaped to receive and retain an optical lens element of the wrap-around or shield type wherein the aperture of the lens outline or edge of at least one surface of the optical lens element is of generally ovaline shape and is located on the surface a sphere whose radius of curvature corresponds to 11 Dioptre (D) or above, a toroid where the horizontal radius or curvature corresponds to 11 D or above, or a surface where the radius of curvature changes across at least one section of the lens aperture.

Such frames differ significantly in curvature from frames known in the prior art.

By the term "an optical lens element of the wrap-around or shield type", we mean that at least one surface of the optical lens falls on a topographical surface that wraps around the human visual apparatus or forms a facial shield.

Preferably the radius of curvature corresponds to 12 D or above, more preferably at least 16 D, most preferably at least 20 D.

The optical lens element may be removably or permanently attached to the frame.

In a preferred form the spectacle frame is itself attached to a sunglass having zero refractive power.

The optical lens element may bear a prescription surface of minus or plus power or may be piano and is preferably suitable for industrial safety or contact sport applications.

The spectacle frame according to this aspect of the present invention may be of any suitable type. The spectacle frame may permit adjustment of the inter-pupillary distance for example via attachment of a lens to the frame supports. Frames of the rimless and temple bar type may be used.

In a preferred form, the front surface of the optical lens element exhibits a change of base curve across the field of vision of the wearer, the base curves being smoothly blended to avoid a prismatic jump in the Rx zone.

By the term "lens element" as used herein, we mean an optical or ophthalmic lens, semi-finished lens, or lens wafer which may be utilised in the formation of an ophthalmic product.

By the term "optical lens element" as used herein, we mean an optical or ophthalmic lens, semi-finished lens or lens formed from a pair of lens wafers which may be utilised in the formation of an optical lens product.

In a preferred embodiment of the present invention, at least one surface of the optical lens element is located on the surface of a toroid where the horizontal radius of curvature corresponds to 11 D or above and the vertical radius of curvature is at least 3 D less than the horizontal curvature.

In a further preferred embodiment where the lens aperture outline falls on a surface, and the radius of curvature changes across a section of the lens aperture, the change in curvature corresponds to 3 D or more. Preferably the change in curvature extends across the entire lens aperture.

In a still further preferred embodiment of the present invention, there is provided a spectacle frame shaped to receive and retain an optical lens element of the wrap-around type wherein the aperture of the lens outline or edge of at least one surface of the optical lens element is of generally ovaline shape and is located on a surface whose radius of curvature varies across the vertical or horizontal sections of the aperture of the lens outline, or both the vertical and horizontal sections thereof.

The change may for example correspond to 3 D or more horizontally and 2 D or more vertically.

The changes in curvature may be distributed smoothly across the aperture of the lens outline. The changes in curvature for example, may occur across the field of direct (forward) vision of a wearer, that is within 55° of the line of sight for distance vision. Alternatively, the change in curvature may occur across the line of sight and within the cone of foveal vision; that is, approximately 25° either side of the line of sight.

In a further alternative, the change of curvature may occur in the off-axis field of binocular vision, that is approximately 25° to 55° either side of the line of sight of the wearer. Still further the change in curvature may occur in the off-axis peripheral field, that is more than 55° away from the line of sight of the wearer.

The changes in curvature may be viewed as asymmetric with respect to the line of sight. For example the curvature may increase in the temporal direction horizontally from nasal limit toward the peripheral viewing field or increase in down gaze vertically from the eye brows to the limits set by nose and cheek intrusion into the visual field. Alternatively the vertical and/or horizontal curvatures remain constant from the line of sight to the visual limits corresponding to brow or nasal intrusion on the visual field. The vertical and/or horizontal curvatures may remain constant from the nasal or brow limits to approximately 25° temporal or down-gaze from the line of sight. For example the temporal curvature is constant to approximately 55° from the line of sight.

In a further preferred aspect, the change in curvature across the aperture of the lens outline is 6 D or more in lens power equivalent, preferably 9 D or more, more preferably 12 D or more.

In a preferred aspect of the present invention, there is provided a spectacle frame shaped to receive and retain an optical lens element of the wrap-around or shield type wherein the aperture of the lens outline or edge of at least one surface of the optical lens element is of generally ovaline shape and remains substantially constant irrespective of lens power.

The spectacle frame may further include a removable or adjustable bridge or nosepiece that accommodates a wearer's interpupillary distance and nasal structure.

In a still further aspect, the present invention provides a spectacle frame shaped to receive and retain an optical lens element of the wrap-around or shield type wherein the aperture of the lens outline or edge of at least one surface of the optical lens element is of generally ovaline shape and exhibits an increased sagittal depth of 10 mm horizontally and/or 5 mm vertically.

The curvature of the frames is accentuated for example relative to known conic or spherical frame designs without tilt.

The spectacle frame may be shaped to receive and retain an optical lens element of the wrap-around or shield type wherein the aperture of the lens outline or edge of at least one surface of the optical lens element is of generally ovaline shape and exhibits a change in sagittal depth across at least a section of the lens aperture of approximately 10 mm horizontally and/or approximately 5 mm vertically.

The change in curvature across the lens aperture is accentuated for example relative to a known conic frame of average curvature.

In a still further aspect of the present invention there is provided a spectacle frame of the wrap-around or shield type, the spectacle frame being shaped to receive and retain an optical lens element including a front and back surface, at least one surface exhibiting a change of base curve cross the field of vision of the wearer.

The optical lens element utilised according to this aspect of the present invention may be mounted directly in a spectacle frame, for example of the wrap around or shield type. When mounted, the optical lens element may be rotated temporally about a vertical axis through the optical centre thereof ("tilt"), or translated so that the line of sight remains parallel to the optical axis of the lens ("offset"), or a combination of both tilt and offset as described below.

In a preferred aspect the optical lens element includes at least a continuous surface and forms a prescription (Rx) zone and a peripheral temporal zone.

Accordingly the spectacle frame is shaped such that the lens element, when mounted, is rotated temporally about a vertical axis through the optical centre thereof.

Alternatively the spectacle frame is shaped such that the lens element, when mounted, is decentred so that the optical axis and direct line of sight remain parallel.

More preferably the spectacle frame is so shaped that the lens element is additionally rotated temporally about a vertical axis through the optical centre thereof.

In a preferred embodiment, the optical lens element includes at least a continuous surface and forming a prescription (Rx) zone and a peripheral temporal zone.

The optical lens element according to this aspect of the present invention may provide prescription (Rx) correction generally in the range of −6.0 D to +6.0 D.

In a preferred aspect, the front surface of the optical lens element exhibits a change of base curve across the field of vision of the wearer, the base curves preferably being smoothly blended to avoid a prismatic jump in the Rx zone. In one embodiment, the base curve from the nasal limit to the optical centre may be relatively low, for example from approximately 0.0 D to approximately 6 D. The base curve from the optical centre to the temporal limit may, in contrast, be a high base curve, e.g. of approximately 6.0 D or above, preferably approximately 12.0 D to 18.0 D.

Preferably, the front and/or back surface(s) of the optical lens element include a compound spherical design to provide the desired prescription (Rx) in the prescription zone. More preferably, this prescription zone will extend across the full aperture of the spectacle frames being employed.

It will be understood that an advantage of the present invention is that a common front curve may be utilised across a range of prescription powers. This provides an improvement in the ease of manufacture of optical lens elements, allows a wide range of prescriptions to be fitted to a single frame design and assists in the reduction of inventories.

In a further preferred aspect the optical lens element in the region from the nasal limit to the optical centre may be generally of the meniscus type. Alternatively, the nasal region of the optical lens element may be biconvex in shape. The biconvex shape is preferred, particularly for lenses of high power, due to its ease of mounting and improved cosmetics for the wearer.

In this form the spectacle frame according to the present invention is shaped to receive and retain an optical lens element including a region of reduced or opposite curvature defining a nasal accentuating region such that facial form in the nasal region is accentuated.

The forward reach of the lenses in the nasal region may be utilized at least in part to provide protection of the wearer's nose from physical impact or radiation damage due to the UV component of sunlight, for example. Lenses having this purpose are desirably curved forward in the nasal region to a horizontal base of 4.0 to 8.0 D so that the combination of lens surface and nose piece of the sunglass frame or unitary lens protects substantially all of the wearer's nose without intruding on the forward visual field.

More preferably the spectacle frame includes an attached nose-piece, such that the lenses and nose-piece together provide physical or radiation protection to the wearer's nose.

The peripheral temporal zone of the optical lens element may be at least in part of generally toric shape. The peripheral temporal zone may be at least in part generally piano.

The peripheral temporal zone may itself form an extension of the prescription zone or may be a non-prescription zone.

In an alternative or additional aspect, the peripheral temporal zone may be modified to permit light control within the zone.

It will be understood that the peripheral temporal zone, for a typical sunglass lens element of the wrap-around type, may for example extend for approximately 10 to 25 mm.

In a further aspect of the present invention, the optical lens element may provide prescription (Rx) correction generally in the range −6.0 D to +6.0 D wherein the front surface is capable of being mounted in a frame of constant design curve irrespective of the Rx, such frame curves being 5.0 D and above; and the back surface provides good clearance from temples or eye lashes; at least one surface exhibits a change of base curve across the field of vision of the wearer.

Preferably the front surface of the lens element has a high compound curve extending from nasal to temporal limits, but the vertical curve is 6.0 D or below.

It will be understood that such vertical curves permit the final prescription lenses, preferably edged lenses, to be adapted to the shape of the wearer's face and so locate closely in a form of the wrap-around type (a so-called "geometrically toric" design for which the vertical curve of the back surface is selected to maintain the desired through power or Rx correction provided by the lens. This may be distinguished from a conventional "optically toric" design wherein one surface is rotationally symmetric and the other is shaped to provide the sphere and cylinder components of the wearer's Rx without consideration of the facial form of a wearer).

Alternatively the optical lens elements may be adapted for mounting in a spectacle frame of the shield type. Accordingly in a still further aspect of the present invention there is provided a spectacle frame of the shield type, the spectacle frame being shaped to receive and retain a unitary optical lens including a pair of optical lens elements, each lens element providing prescription (Rx) correction generally in the range −6.0 D to +6.0 D wherein the front surface is capable of being mounted in a frame of constant design curve irrespective of the Rx, such frame curves being 5.0 D and above; and the back surface provides good clearance from temples or eye lashes; at least one surface exhibits a change of base curve across the field of vision of the wearer.

The optical lens element may, when mounted in a spectacle frame, be rotated temporally about a vertical axis through the optical centre thereof or decentred, or both rotated and decentred.

Such complex surfaces cannot be created by conventional ophthalmic lens processing equipment, but may be generated by current state of the art surfacing equipment such as the "Ultralab" unit from Micro Optics Inc. This equipment produces a precise surface form by cutting to a computer generated file. The final optical finish may be achieved by applying an overlay coat of optical resin matching the refractive index of the underlying lens. Errors which would be created by polishing the generated surface are thereby avoided or at least substantially reduced.

The front surface of this semi-finished optical lens element has a precise orientation corresponding to the horizontal plane in which tilt and offset may occur. Therefore it may bear other optical features which require precise orientation with respect to vertical and horizontal directions. Examples of these are multifocal power addition for near or intermediate visual distances (both conventional segment type and progressive addition lenses), polarising filters, or cosmetic mirror or tint treatments.

The peripheral temporal zone of the optical lens element according to the present invention may be constructed to maximise cosmetic appearance. Ideally, the peripheral temporal zone should show little or no optical difference from the remainder of the front surface of the ophthalmic lens element. For example, where the prescription Rx surface of the ophthalmic lens is a minus Rx lens, the temporal extension may exhibit a zero refractive power or positive refractive power. The temporal extension may be tapered in cross-section to maximise cosmetic acceptability.

Accordingly, in a preferred aspect the curvature of the front surface is modified in the peripheral temporal zone to substantially correspond to the curvature of the back surface thereof.

It will be understood that the peripheral temporal zone thus formed is a substantially piano extension.

The present invention will now be more fully described with reference to the accompanying figures and examples. It should be understood, however, that the description following is illustrative only and should not be taken in anyway as a restriction on the generality of the invention described above.

DETAILED DESCRIPTION OF THE DRAWINGS AND EXAMPLES

Example 1

Figure 1:
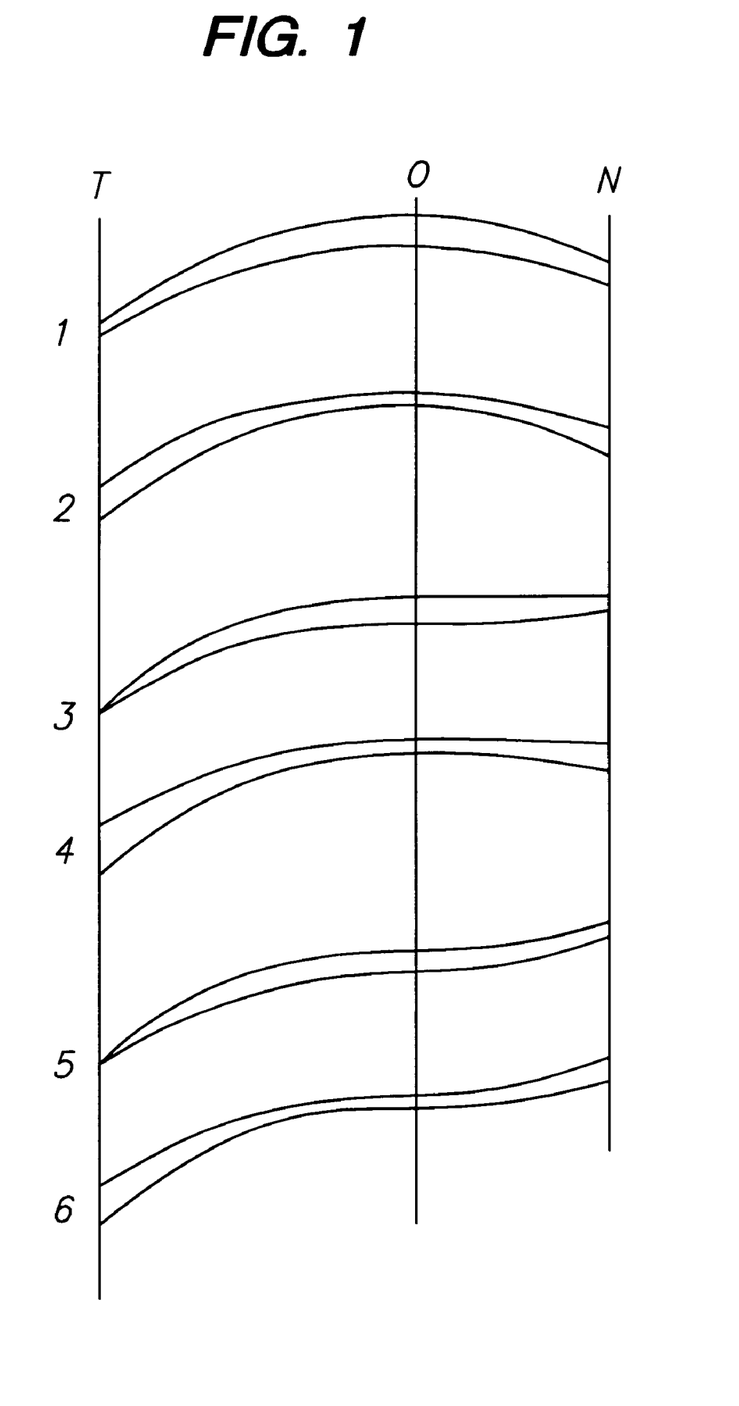
FIG. 1 is a series of horizontal sections of prescription lenses of various contours.

FIG. 1

Lenses which may be included in frames giving various degrees of wrap toward the temples, the front curves preferably being independent of the Rx to suit either a simple range of sunglass frames or of internal frames to be attached to a visor assembly. (FIG. 1 lenses 3 and 4). Such visor assembly may be a simple shield or a shield with separate temple pieces.

Example 2

FIG. 1 depicts lenses (5 and 6) which may be included in products accentuating facial form at the nose as well as temples, such as glazed lenses or complementary lens elements for shields. Shields may be clear sports shields designed solely to protect the face in ball sports such as basketball, where the activity precludes heavy helmets and the like used for example for American football. Alternatively they may provide UV protection, guarding against skin cancer as is experienced commonly on individuals noses.

In FIG. 1 there is depicted the horizontal section of Rx lenses whose optical axis O is located closer to the nasal limit N than the temporal limit T. Lenses 1 and 2 are conventional spheres with front and back base curves of 6 D and 8 D to produce Rx lenses of plus and minus 2 D.

Lenses 3 and 4 have the same 6 and 8 D spherical base curves from temple T to optical axis O. Toward the nasal limit, both lenses have flat front curve of approximately 0 D. The plus Rx lens 3 has negative back surface curve to provide the required refractive power. These lenses give maximum temporal reach for lenses of conventional cosmetic appearance whilst also having least curvature of the temporal design. A full Rx range is preferably designed with a constant front surface form. However physical requirements for lens clearance at temporal and nasal limits may dictate that lower design curve power be used for higher minus Rx lens categories.

Lenses 5 and 6 have the same spherical design toward the temples as other lenses in this figure. However, the curves from optical axis O to nasal limit N are negative in each instance.

These last lenses have a distinctive shape and reach forward toward the nasal bridge as well as back to the temples. They may be manufactured with general conic orthogonal curves approximately 6 to 9 D or so and are most obviously useful for creating eyewear which accentuates the contours of the face including the nasal region. This could be for sunwear but also applies to sports visors such as basketball visors where a safety shield fits closely around the face to protect temples, cheeks and the nose. The lenses designed on the principle of 5 and 6 in FIG. 1 satisfy the purpose of such an application. The front curve can be chosen independent of the Rx.

Example 3

Figure 2:
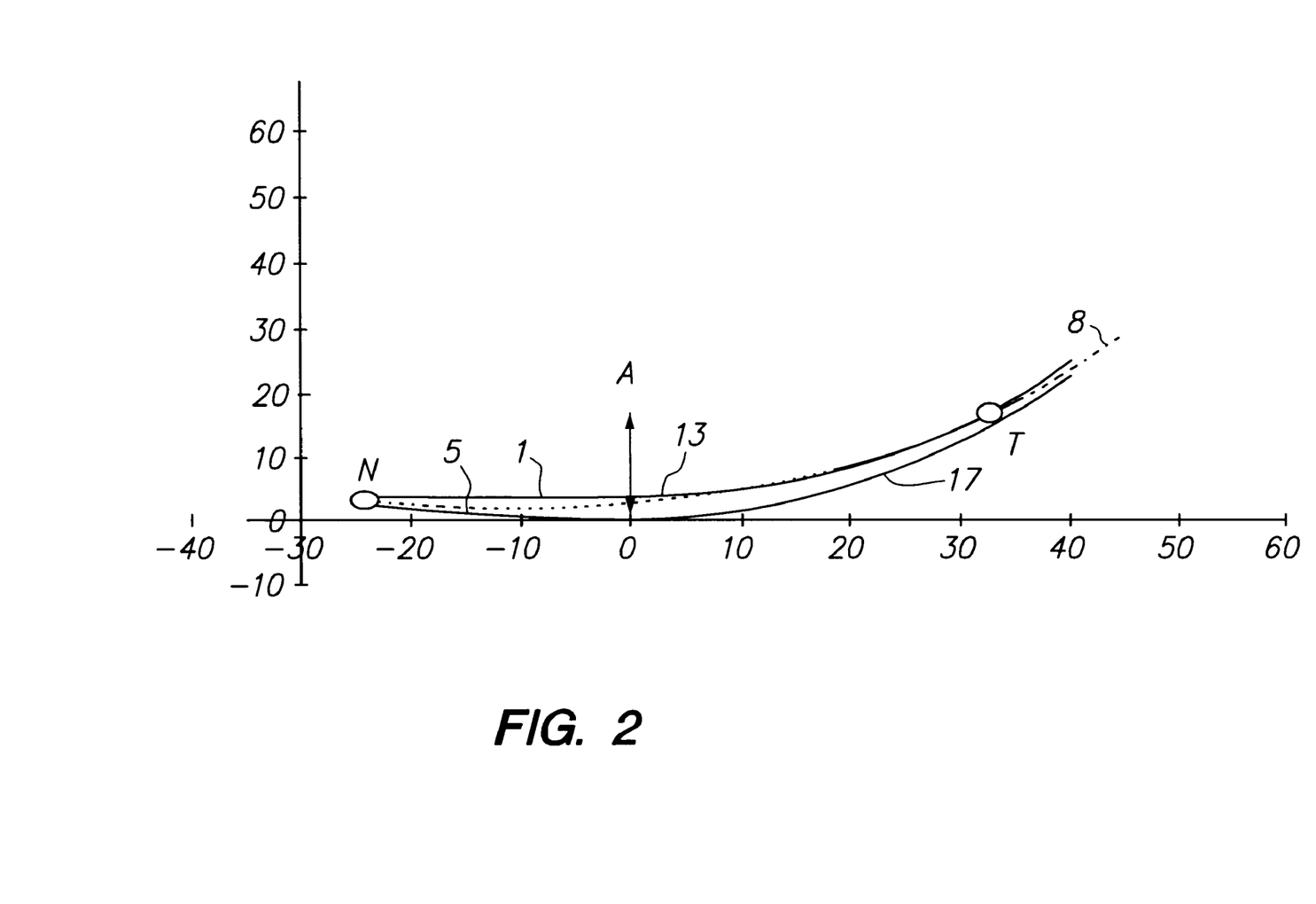
FIG. 2 illustrates the horizontal section of a +4.0 D optical lens which may be used with the spectacle frames according to the present invention.

FIG. 2

FIG. 2 illustrates the horizontal section of a +4.0 D optical lens according to the present invention. This lens may be glazed directly into a frame with nominal design curve of 8 D. In this case, the front curve toward the temple T is 17 D and that toward the nasal limit N is 5 D. There is no piano region and the lens provides the desired Rx correction across its entire aperture.

Example 4

A: refer to FIG. 2 above

The lens depicted therein has front and back surfaces which are smooth and continuous, in surface height and surface shape. Together, the pair of surfaces define a constant through refractive power although the curvature of each has a discontinuity in the horizontal plane across the optical axis of the lens. The curvature change is identical for both surfaces, thus providing constant refractive power through the lens.

Either surface will not function as a suitable lens surface sheet unless mated with a complementing surface. A suitable mathematical form for the surfaces is $$Z(x, y) = 1/2A_2 - \sqrt{(1 - 2A_2 - Z(x))^2 - y^2}$$

$$\text{where } Z(x) = \sum_n B_n x^n$$

and Ox is the horizontal direction while Oy is the vertical direction. The coefficient $A_2$ has a constant value specifying a constant vertical curvature, while the coefficients $B_n$ take different values for positive and negative values of x.

For the lens in FIG. 2 made in polycarbonate, the front surface is $A_2$=6.838 E-03, and $B_2$=14.530 E-03 for $x \geq 0$ and $B_2$=4.274 E-03 for $x<0$ while $B_4=(B_2)^3$, $B_6=2*(B_2)^5$, $B_8=5*(B_2)^7$ For the back surface, $A_2$=3.419 E-03 and $B_2$=11.111 E-03 for $x \geq 0$ and $B_2$=0.855 E-03 for $x<0$.

Moulds for injection molding or casting of such lenses are produced by the procedures used in making progressive addition lenses, either by CNC milling of metal tools or of ceramic formers from which to manufacture glass tools (moulds) for casting. Preferably the surface is milled via a succession of traverses in the Oy direction of the design, these being indexed horizontally to follow the profile Z(x). This limits the sources of error in imparting the change in surface form corresponding to the values of $B_2$ for positive and negative values of x.

The remaining challenge in lens manufacture is to ensure precise alignment of axis and orientation of the two mould surfaces with respect to each other. Misalignment will cause errors in refractive power at the vertical axis.

Convention in the ophthalmic industry is to blend one surface region into another abutting region of different character in order to ensure that unwanted cosmetic features such as localised surface reflections are avoided. Typically this has been achieved with localised errors in refractive power. With modem CNC machining technology, such power errors can be avoided. It has been found that the two parts of the lens depicted in FIG. 2 (i.e. $x \geq 0$ and $x>0$) may be blended together such that the conformity of one to the other is heightened. Specifically, the surfaces and both first and second derivates may be rendered smooth and continuous in themselves. Furthermore, the relationship between the surfaces will still define a constant refractive power through the lens.

Two examples are provided:

Example 4A

To blend the two lens segments over a zone of width 8 mm to the nasal side of the line of direct sight.

$$Z(x) = B'_0 + \sum_{n=1}^{4} B'_{2n} x^{2n}; \quad x \leq x_0$$

$$= \sum_n B_n x^n; \quad x_0 < x \leq 0$$

$$= \sum_{n=1}^{4} B''_{2n} x^{2n}; \quad x > 0$$

where $x_0$=-8.0; $B'_0$=0.220225

Figure 3:
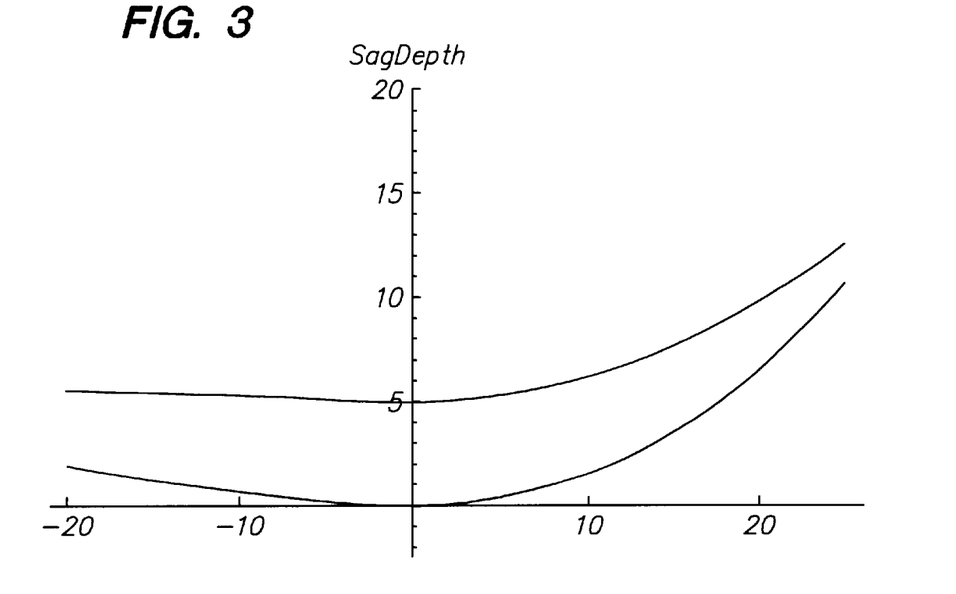
FIG. 3 is a horizontal section of a lens element.
Figure 4:
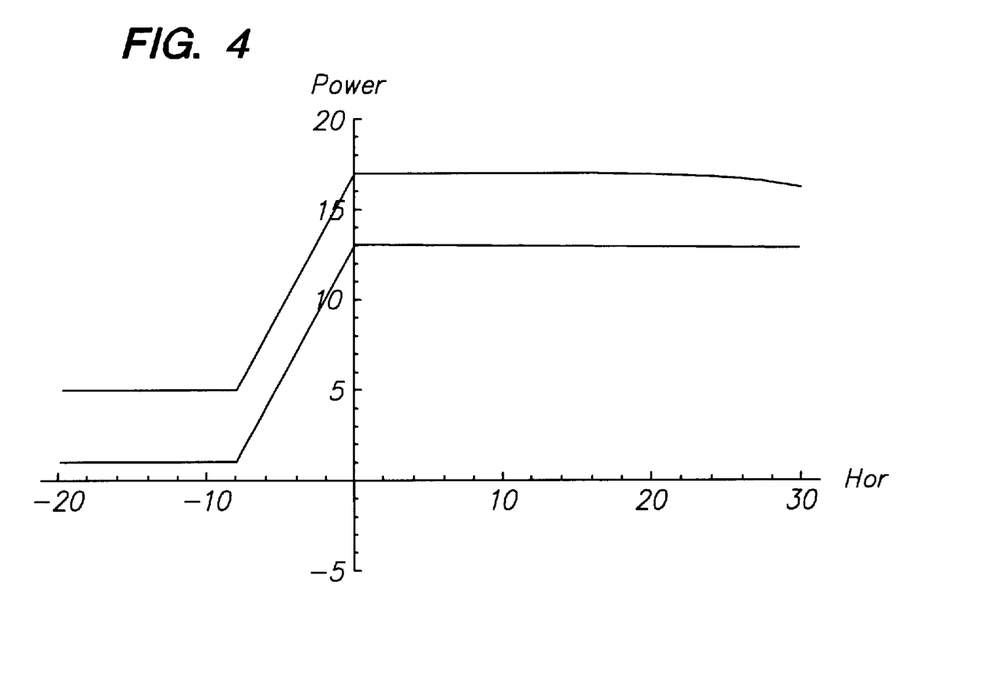
FIG. 4 is a plot of the horizontal sagittal power of the lens element of FIG. 3.

$B'_2$=4.274 E-03; $B'_4$, $B'_6$, $B'_8$ as above $B''_2$=14.530 E-03; $B''_4$, $B''_6$, $B''_8$ as above and $B_2=14.530$ E-03+x*4.273E-04, $B_{2n}$ as above for the front surface For the back surface, $x_0=-8.0$; $B'_0=0.218973$ $B'_2=11.111$ E-03; $B'_{2n}$ as above $B''_2=0.855$ E-03; $B''_{2n}$ as above and $B_2=11.111$E-03+x*4.273E-04, $B_{2n}$ as above This creates the horizontal section shown here as FIG. 3 for which the horizontal horizontal power of the two surfaces vary as for FIG. 4. Note the linear change of horizontal power across the blend zone with absence of discontinuities in the surface description and its shape and curvature features.

Example 4B

To blend the lens segments within 6 mm, using a non-linear change in horizontal power.

Figure 5:
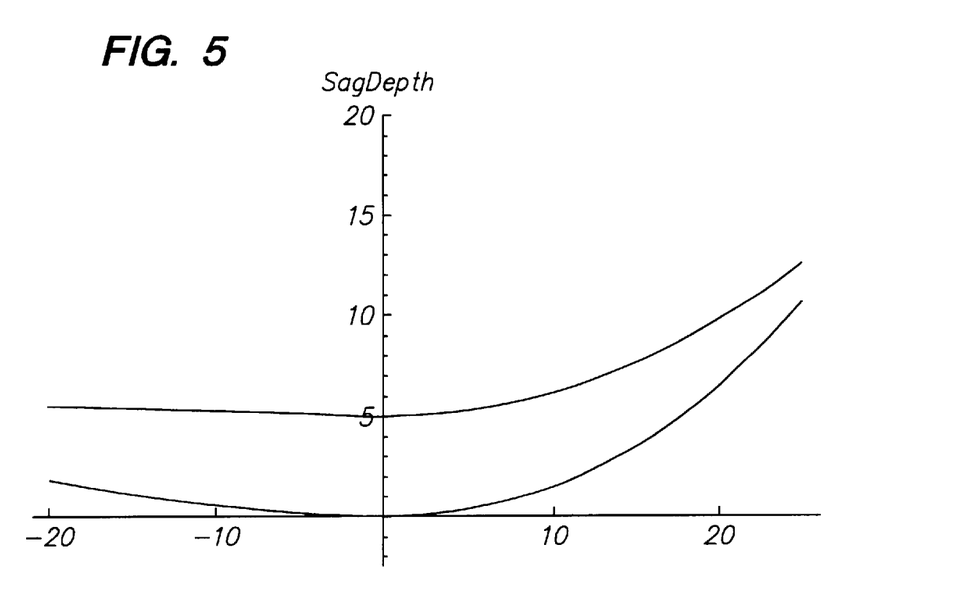
FIG. 5 is a plot of the horizontal section of another lens element.
Figure 6:
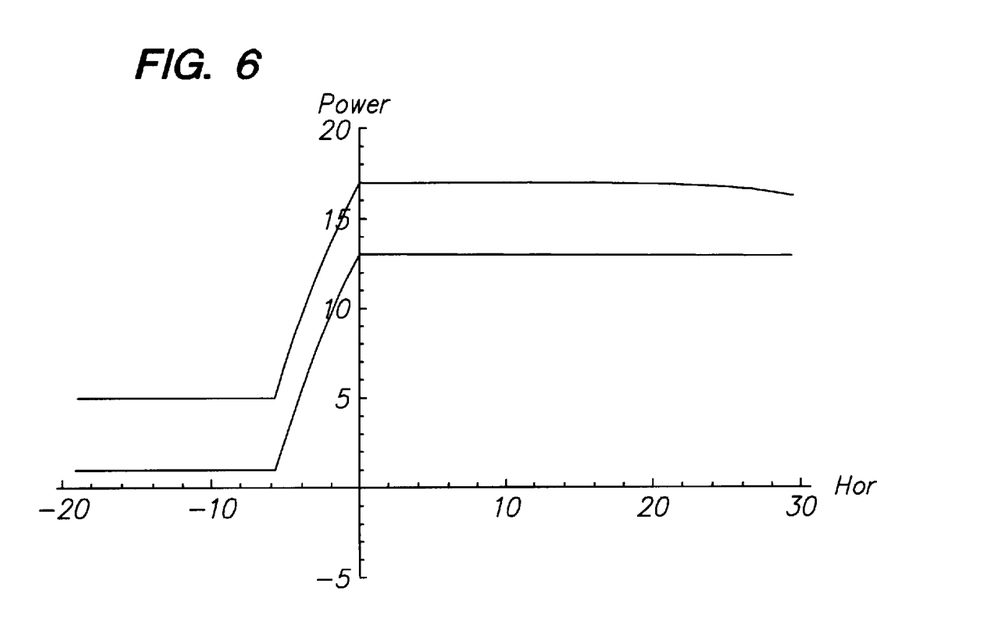
FIG. 6 is a plot of the horizontal sagittal power of the lens element of FIG. 5.

The lens section of FIG. 5 herein and the horizontal power changes of FIG. 6 herein are achieved by the following changes to the parameters for Example 4 above:

$x_0=-5.775$; $B'_0=0.130382$ (front); $B'_0=0.130013$ (back)

and for the front surface;

$B_2=14.503$E-03+x*4.273E-04-$x^2$*2.851E-05, $B_{2n}$ as above while the back surface has $B_2=11.111$E-03+x*4.273E-04-$x^2$*2.851E-05, $B_{2n}$ as above

Example 5

Figure 7A:
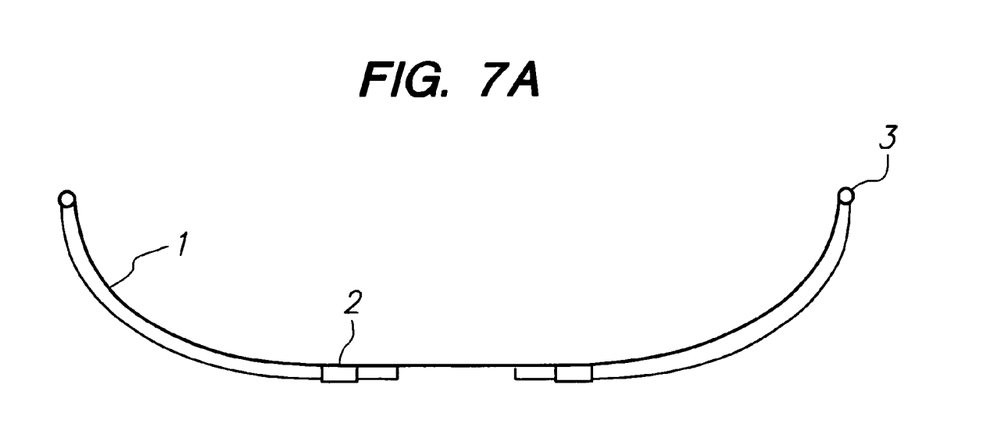
FIGS. 7A and 7B illustrate a top schematic view and tilted schematic view of a pair of sunglasses including a spectacle frame according to the present invention.
Figure 7B:
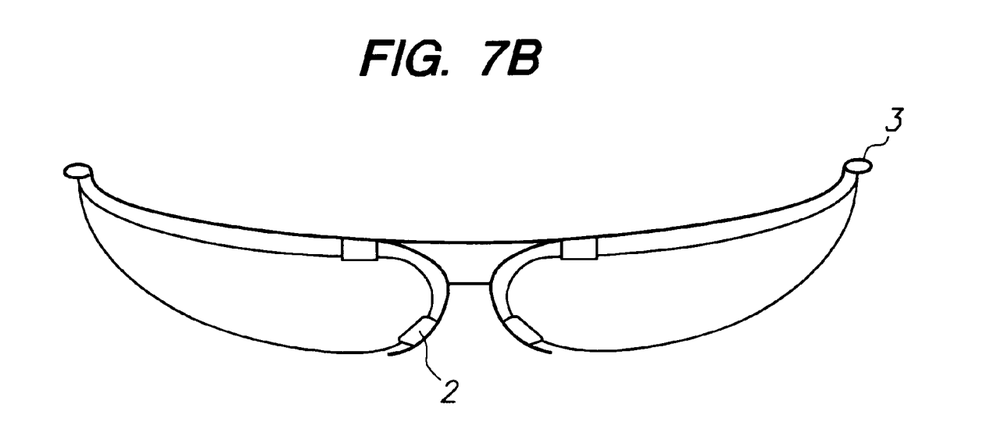

FIGS. 7A and B illustrate a top schematic view and tilted schematic view of a pair of sunglasses including a spectacle frame according to the present invention.

The curvature of the frame in the horizontal plane (1) increases from a relatively low value at the nasal limit of a lens fitted to the spectacle frame to a relatively high value at the temporal limit (3). Each lens is attached to the frame by a set of three lugs (2).

Example 6

Figure 8:
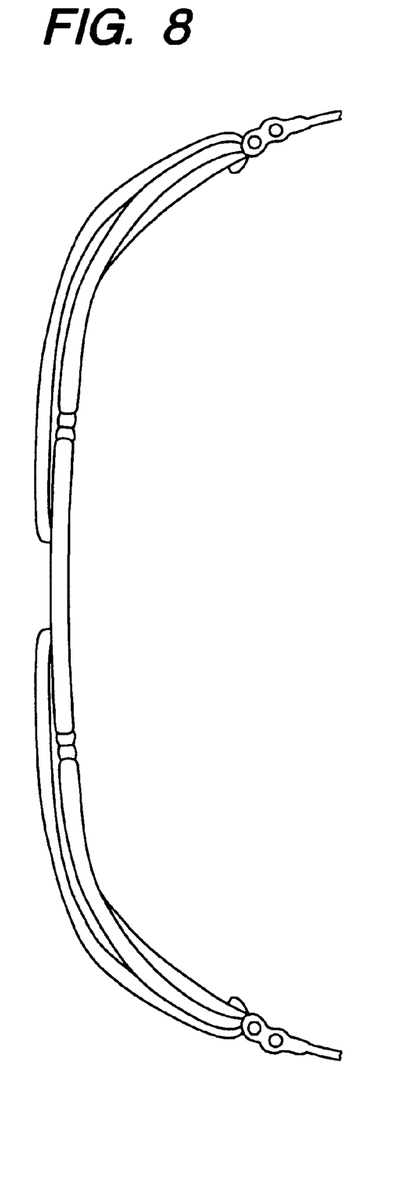
FIG. 8 illustrates a top view of a pair of eyeglasses including a spectacle frame according to the present invention.

FIG. 8 illustrates a top view of a pair of eyeglasses including a spectacle frame according to the present invention. The spectacle frame is characterised in that the aperture of the lens outline is ovaline in shape.

The spectacle frame is designed to receive and retain a pair of optical lenses wherein the lens curvature increases from nasal to temporal limit. In this example, the lens base curve corresponds to 0 D at the nasal limit and 18 D at the temporal limit.

Example 7

Figure 9:
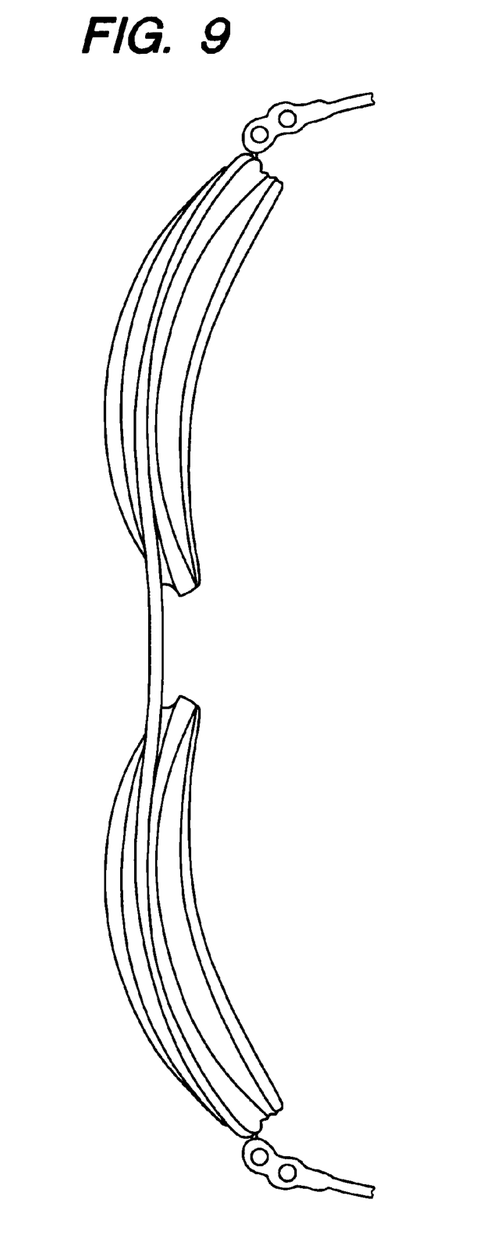
FIG. 9 illustrates a top view of a pair of eyeglasses including a spectacle frame according to the present invention.

FIG. 9 illustrates a top view of a pair of eyeglasses including a spectacle frame according to the present invention. The spectacle frame is characterised in that the aperture of the lens outline is ovaline in shape.

The spectacle frame is designed to receive and retain a pair of optical lenses whose front surfaces have a base curve of 16 D.

Finally, it is to be understood that various other modifications and/or alterations may be made without departing from the spirit of the present invention as outlined herein.

What is claimed is:

1. A spectacle frame shaped to receive and retain an optical lens element of the wrap-around type for engaging the edge of the optical lens element wherein a lens engaging portion of the frame is of generally ovaline shape and is located on the surface of a toroid having a horizontal radius of curvature of at least 12 D.

2. A spectacle frame according to claim 1, wherein the radius of curvature corresponds to 16 D or above.

3. A spectacle frame according to claim 2, wherein the radius of curvature corresponds to 20 D or above.

4. A spectacle frame of claim 1, wherein the surface of the toroid corresponds to the front surface of the optical lens element.

5. A spectacle frame according to claim 4, wherein the vertical radius of curvature of the toroid is at least 3 D less than the horizontal curvature.

6. A spectacle frame shaped to receive and retain an optical lens element of the wrap-around type for engaging the edge of the optical lens element wherein a lens edge engaging portion of the frame is generally ovaline shaped and is located on a surface wherein a radius of curvature of said surface changes across at least one section of the lens aperture and wherein the maximum horizontal radius of curvature is at least 12 D.

7. A spectacle frame according to claim 1, wherein changes in curvature are distributed smoothly across the aperture of the lens outline.

8. A spectacle frame according to claim 1, wherein the change in curvature occurs across the field of direct (forward) vision of a wearer.

9. A spectacle frame according to claim 1, wherein the change in curvature occurs across the line of sight and within the cone of foveal vision.

10. A spectacle frame according to claim 1, wherein the change in curvature occurs in the off-axis field of binocular vision.

11. A spectacle frame according to claim 10, wherein vertical and/or horizontal curvatures remain constant from the line of sight to the visual limits corresponding to brow or nasal intrusion on the visual field.

12. A spectacle frame according to claim 10, wherein vertical and/or horizontal curvatures remain constant from the nasal or brow limits to approximately 25° temporal or down-gaze from the line of sight.

13. A spectacle frame according to claim 1, wherein the changes in lens curvature are asymmetric with respect to the line of sight.

14. A spectacle frame according to claim 13, wherein curvatures increase in the temporal direction horizontally from the nasal limit toward the peripheral viewing field.

15. A spectacle frame according to claim 14, wherein temporal curvature is constant to approximately 55° from the line of sight.

16. A spectacle frame according to claim 13, wherein curvatures increase in down gaze vertically from the eye brows to the limits set by the nose and cheek intrusion in to the visual field.

17. A spectacle frame according to claim 1, wherein the change in curvature across the aperture of the lens outline is 6 D or more in lens power equivalent.

18. A spectacle frame according to claim 17, wherein the changes in curvature across the aperture of the lens outline is 9 D or more in lens power equivalent.

19. A spectacle frame according to claim 18, wherein the change in curvature across the aperture of the lens outline is 12 D or more in lens power equivalent.

20. A spectacle frame according to claim 1, wherein the optical lens elements are removably or permanently attached to the frame.

21. A spectacle frame according to claim 20, wherein the spectacle frame is itself attached to a sunglass having zero refractive power.

22. A spectacle frame according to claim 20, wherein the optical lens element has corrective power.

23. A spectacle frame according to claim 20, wherein the frame is suitable for industrial safety or contact sport applications.

24. The spectacle frame of claim 1, wherein the surface of changing radius of curvature corresponds to the front surface of the optical lens element.

25. A spectacle frame according to claim 24, wherein the change in curvature corresponds to 3 D or more across the at least one section of the aperture of the lens.

26. A spectacle frame according to claim 25, wherein the change in curvature extends across the lens aperture.

27. The spectacle frame of claim 1, wherein the maximum radius of curvature is at least 16 D.

28. The spectacle frame of claim 27, wherein the maximum radius of curvature is at least 20 D.

29. The spectacle frame of claim 1, wherein the radius of curvature varies in both the vertical and horizontal directions.

30. A spectacle frame according to claim 29, wherein the change in curvature corresponds to 3 D or more horizontally and 2 D or more vertically.

31. A spectacle frame shaped to receive and retain a pair of optical lens elements wherein the frame includes rim portions surrounding ovaline outlines of the pair of lens elements, wherein the rim portions each correspond to edges of the respective lens surfaces, and wherein each surface is a toroid surface which exhibits a sagittal depth of at least 10 mm horizontally.

32. A spectacle frame shaped to receive and retain a pair of optical lens elements wherein the frame includes rim portions surrounding ovaline outlines of the apertures of the pair of lens elements, wherein the rim portions each correspond to edges of the respective lens surfaces, and wherein each surface exhibits a change in curvature across the respective lens aperture and each surface exhibit a sagittal depth of at least 10 mm horizontally.

33. A spectacle frame according to claim 32, wherein the optical lens elements include at least a continuous surface and forms a prescription (Rx) zone and a peripheral temporal zone.

34. A spectacle frame according to claim 31, the spectacle frame being shaped such that each lens element, when mounted, is rotated temporally about a vertical axis through the optical center thereof.

35. A spectacle frame according to claim 31, the spectacle frame being shaped such that each lens element, when mounted, is decentered so that the optical axis and direct line of sight remain parallel.

36. A spectacle frame according to claim 35, the spectacle frame being shaped such that each lens element is also rotated temporally about a vertical axis through the optical center thereof.

37. A spectacle frame according to claim 31, the spectacle frame being shaped to receive and retain optical lens elements that each include a region of changed curvature defining a nasal accentuating region such that facial form in the nasal region is accentuated.

38. A spectacle frame shaped to receive and retain a unitary optical lens including a pair of optical lens elements, each lens element providing prescription (Rx) correction generally in the range −6.0 D to +6.0 D wherein a front surface is capable of being mounted in a frame of constant design curve irrespective of the Rx, such frame curves being 5.0 D and above; and a back surface provides good clearance from temples or eye lashes, and at least one surface exhibits a change of base curve across the field of vision of the wearer.

39. A spectacle frame according to claim 38, the spectacle frame being shaped such that each lens element, when mounted, is rotated temporally about a vertical axis through the optical center thereof.

40. A spectacle frame according to claim 38, the spectacle frame being shaped such that the lens element, when mounted, is decentred so that the optical axis and direct line of sight remain parallel.

41. A spectacle frame according to claim 40, the spectacle frame being shaped such that the lens element is additionally rotated temporally about a vertical axis through the optical centre thereof.

* * * * *